United States Patent [19]

Douwens et al.

[11] Patent Number: 5,148,801

[45] Date of Patent: Sep. 22, 1992

[54] ELECTRONIC HEATER-HUMIDIFIER FOR HYPOTHERMIA TREATMENT

[75] Inventors: Robert J. Douwens, Quathiaski Cove; John S. Hayward, Victoria, both of Canada

[73] Assignee: University of Victoria, Victoria, Canada

[21] Appl. No.: 499,941

[22] Filed: Mar. 23, 1990

[51] Int. Cl.$^5$ .................. A61M 16/10; A61M 15/00; A62B 7/00; A62B 18/02

[52] U.S. Cl. .................. 128/203.16; 128/203.26; 128/204.17; 128/203.29; 128/204.13; 128/203.17; 128/203.27

[58] Field of Search .................. 128/203.16, 203.17, 128/203.26, 203.27, 204.17, 204.13, 203.29

[56] References Cited

U.S. PATENT DOCUMENTS

| | | | |
|---|---|---|---|
| 2,519,515 | 8/1950 | Turner | 128/203.27 |
| 3,770,938 | 11/1973 | Agarate | 128/204.17 |
| 3,954,920 | 5/1976 | Heath | 128/203.27 |
| 3,983,869 | 10/1976 | Suzuki | 128/204.13 |
| 4,248,217 | 2/1981 | Brisson | 128/204.17 |
| 4,288,396 | 9/1981 | Ottestad | 128/204.17 |
| 4,319,566 | 3/1982 | Hayward et al. | 128/204.17 |
| 4,369,777 | 1/1983 | Lwoff et al. | 128/204.17 |
| 4,621,633 | 11/1986 | Bowles et al. | 128/204.17 |
| 4,652,408 | 3/1987 | Montgomery | 128/204.13 |
| 4,662,352 | 5/1987 | Aviles, Jr. | 128/204.17 |
| 4,825,863 | 5/1989 | Dittmar et al. | 128/204.17 |
| 4,829,997 | 5/1989 | Douwens et al. | 128/204.17 |

Primary Examiner—Edgar S. Burr
Assistant Examiner—Kimberly L. Asher
Attorney, Agent, or Firm—Harry M. Weiss

[57] ABSTRACT

A portable, battery-operated (e.g. 12 v.) electronic heater/humidifier is provided for hypothermia treatment. This heater/humidifier includes the combination of a casing provided with a heat exchanger system comprising an upper compartment loaded with a tangled mass of high heat conductivity material, and, serially-interconnected thereto, at least two serially-interconnected lower compartments, each such lower compartment being open at the bottom to a water reservoir and containing a lower horizontally-oriented heater element for heating water in the water reservoir and an upper porous hydrophilic batt. An airflow path is established between an air inlet and an air outlet, providing a one-way-flow airway system first through the tangled mass of high heat conductivity material, to transfer heat obtained conductively from the heater elements for preheating the incoming air and then through the porous hydrophilic batts, for wicking action of heated water to the site of vaporization in the air flow path. An inhalate thermal sensor is located within the air stream of the air outlet, for continuously monitoring the temperature of that air stream. A heater control is also provided, the heater control including a high-limit thermal sensor to control the heating power to the heaters, dependent on the temperature sensed by the inhalate thermal sensor.

14 Claims, 2 Drawing Sheets

ELECTRONIC HEATER-HUMIDIFIER FOR HYPOTHERMIA TREATMENT

BACKGROUND OF THE INVENTION (i) Field of the Invention

This invention relates to an electronic heat-exchanger in the form of a novel device for providing heated and humidified air from a flow of air, passing a heat source, which device is especially useful for inhalation warming of hypothermia victims.

(ii) Description of the Prior Art

Hypothermia is one of the most frequently encountered and yet often overlooked aspects of emergency medicine. Hypothermia, like other medical conditions, is graduated by the degree of severity and the symptoms and urgency of treatment may differ radically at different levels. In mild hypothermia above about 35° C. (about 95° F.), the accepted treatment is passive rewarming by natural or endogenous heat generation, which is simple, requires no equipment (other than a warm environment and/or blanket), and has no inherent morbidity. Moderate hypothermia occurs in the range of about 32° to about 35° C. (about 89.6° to about 95° F.) and may produce loss of motor control, slurred speech and amnesia; serious hypothermia occurs at body core temperatures below about 32° C. (about 89.6° F.) and is indicated by muscle rigidity, peripheral cyanosis and shock; and severe hypothermia occurs at temperatures from about 25° to about 28° C. (about 77° to about 82.4° F.) at which the victim may have lost deep tendon reflexes and suffer ventricular fibrillation and may appear dead with no palpable pulse or audible heartbeat. Body temperatures below about 25° C. (about 77° F.) cause cardio-pulmonary arrest and death. These forms of hypothermia clearly present life-threatening medical problems complicating the treatment of the victim.

It is becoming established that the safest and most efficient technique for treating the severely hypothermic victim is by active core rewarming, i.e. the delivery of heat primarily to the body core or central circulation system (and also avoiding simultaneous rapid rewarming of the skin and extremities). Of several methods, only inhalation rewarming is suitable for use by paramedics and other trained emergency rescue personnel at a rescue site or during transport to hospital or clinical facilities.

Warm, moist air is also very useful for relieving laryngectomy and tracheotomy patients, and to relieve asthmatic bronchial spasms.

In the normal breathing process, inhaled air becomes warmed and humidifies as it passes through the nasal, tracheal and bronchial passages. This basic body function protects the delicate membranes in the lungs, but may not be sufficiently effective in heavy or rapid breathing of very cold dry air. During exhalation, some heat and moisture is returned to the walls of the breathing passages, but most of the heat energy and moisture is lost in the exhaled gases.

At rest and at a comfortable room temperature, the energy loss is of the order of about 1 Kcal per hour, and is easily compensated by normal body heat production. However, at low temperatures and high altitudes, the energy loss could be about 230 Kcal and about 250 grams of water per hour. This is a significant portion of the energy output of the body and contributes to the harmful effects caused by the inhalation of extremely cold air. In the absence of the ingestion of food, the mere use of warm clothing may not be sufficient to retain a desirable amount of the energy. Also, since thirst response is suppressed by extreme cold, desiccation could become a problem.

There is thus a widespread need for apparatus capable of producing heated and moist air, and in most cases such need is for air heating apparatus which is self-contained and not requiring large amounts of electric power, and which is compact, safe and not needing a flame to heat the air, and lightweight so as to be conveniently portable. As discussed above, one important current need for such air heating apparatus is to produce heated air to be inspired by persons through a suitable device into the lungs, which is an efficient means for warming persons suffering from body core heat loss that has reached the stage of hypothermia. Such inspiration of heated air directly into the airways and lungs is the most effective and safe way to stabilize and rewarm a person, and to bring hospital-type treatment to the rescue situation.

A number of devices have been developed in the prior art for the purpose of reducing the harmful or dangerous effects caused by the inhalation of extremely cold air. Many patented devices and techniques for heating and humidifying breathing gases have been devised for many purposes.

It is well known in inhalation therapy that gases which are to be delivered to a subject or patient should be humidified and warmed prior to inhalation by the subject. Exemplary of the type of gases delivered to a patient include oxygen as well as a mixture of air and oxygen.

Various types of systems have been proposed for generating humidifying gases, generally for use on connection with respiratory care systems. For example, one type of humidification unit includes a chamber suitable for containing a quantity of water, the bottom wall thereof having a heater plate associated therewith. An aluminized insert element is provided which is constructed in the form of a spiral within the chamber. Between the concentric loops of the spiral a sheet of absorbent paper is positioned in loose fitting relationship, the absorbent paper being manually fed into the spiral until the same is present between all of the concentric loops of the spiral. The aluminum element functions to conduct heat from the lower heater plate upwardly while the absorbent paper functions to take water up by capillary action thereby to provide moisture throughout the spiral assembly. A gas is injected into the unit and must be specifically directed to the open end of the spiral with the necessity that the gas completely pass through the open concentric circles of the spiral and exit from the innermost portion of the spiral upwardly to a gas outlet and from there into an outlet tube for delivery to a subject.

U.S. Pat. No. 3,954,920 patented May 4, 1976 by W. I. Heath provided a gas humidification system including a substantially closed chamber formed by a plurality of side walls, a bottom wall and a top wall having a gas inlet and outlet ports associated therewith, and heat means associated with the bottom wall. A humidification element was removably positionable within the chamber. That element included a heat conductive metallic member having an end for contact with the heat means and extending upwardly therefrom, and a layer of water absorbent material fixedly secured to at least one of the surfaces of the metallic member. The metallic member presented a multi-faceted surface and the absorbent material paralleled the multi-faceted surface of the body portion of the metallic member thereby presenting an increase surface area for gas to pass over and around the humidification element at elevated temperatures. This was said to increase the relative humidity of the gas prior to inhalation by a patient.

U.S. Pat. No. 3,912,795 patented Oct. 14, 1975 by R. R. Jackson provides an apparatus for humidifying a gas and delivering it to be breathed. The apparatus included a gas chamber having an inlet for communication with a source of the gas, an outlet, and a water chamber coextensive over a zone with a portion of the gas chamber. One of the chambers had a wall which was permeable to water vapour at the zone. Water was brought into intimate contact with one side of the wall at the zone at a vapour pressure sufficient to cause passage of water vapour through the wall and into the gas chamber to humidify gas therein. The apparatus included water return and supply tubes effectively sealed to the water chamber and arranged for respective connection to a source of vacuum and to a water reservoir exposed to atmospheric pressure.

U.S. Pat. No. 4,026,285 patented May 31, 1977 by R. R. Jackson provided a humidifier for air or gas flow to the lungs to heat the air flow and to saturate it with water vapour. Heated water injected into a humidifying passage flows down multiple paths in the gas stream. Heating of the water is done on a localized basis at sterilizing temperature while over-all temperature is kept lower using a heater combined with the pump of the injection line. All surfaces of the humidifier are exposed to the water. The gas outlet connection communicates with a space between the water paths and the reservoir, and is directed toward the reservoir. The humidifying passage is a tubular column holding a mass of tangled inert filaments.

U.S. Pat. No. 4,038,980 patented Aug. 2, 1977 by I. Fodor provided an air humidifier for a surgical breathing machine which had an evaporating chamber containing a temperature regulated low thermal mass heater. A water drip feed unit dripped water onto a sheath of porous material of the heater at a predetermined rate. The water was substantially completely and instantaneously evaporated to create an air temperature and relative humidity within predetermined limits. The heater temperature and water supply rate had manual adjustment means coupled together so that such predetermined limits were not exceeded. The evaporating chamber was tubular and was of similar cross section to inter- connecting conduits so as not unduly to interfere with pressure waves from the breathing machine.

SUMMARY OF THE INVENTION (i) Aims of the Invention

It is seen that the above prior art does not provide a portable device that heats and humidifies air as it is drawn through a heated environment and through a source of water, and in which that optimum temperature of the air is thermostatically controlled.

One object of the present invention then is to provide a device for the inhalation rewarming of hypothermic victims while avoiding further cooling of the body core.

Another object of the present invention is to provide such a device which is highly portable and which would be lightweight and inexpensive to construct.

Yet another object of this invention is to provide such a device which includes good insulation against heat loss to the environment.

Still another object of this invention is to provide such a device in which a porous material is used to facilitate transfer of water vapour to the inhalate.

Still another object of this invention is to provide such a device which is designed to provide an inhalate of the desired therapeutic temperature (in the range of about 40° C. to about 45° C.) by means of thermostatically-controlled means.

(ii) Statement of Invention

By one broad aspect of this invention an electronic heater/humidifier is provided for hypothermia treatment. The heater/humidifier includes a casing provided with: (a) a heat exchanger system comprising an upper compartment loaded with a tangled mass of high heat conductivity material, and, serially-interconnected thereto, at least two serially-interconnected lower compartments, each such lower compartment being open at the bottom to a water reservoir and containing a lower, horizontally-oriented, water- and air-porous heater element for heating water in the water reservoir, and an upper porous hydrophilic batt; (b) an airflow path between an air inlet and an air outlet, providing a one-way-flow airway system, first through the tangled mass of high heat conductivity material, to transfer heat obtained conductively from the heater elements for preheating the incoming air and then through the porous hydrophilic batts, for wicking action of heated water to the site of vaporization in the air flow path; (c) an inhalate thermal sensor located within the air stream of the air outlet for continuously monitoring the temperature of that air stream; and (d) a heater control including a high-limit thermal sensor to control the electric power to the electric heaters dependent on the temperature sensed by the inhalate thermal sensor.

(iii) Other Features of the Invention

The air flow path preferably includes an upper forward direction through the upper compartment, and a lower, reverse direction air flow path through the lower compartments. The upper air flow path is separated from the lower air flow path by a non-porous, heat-conducting member, the non-porous, heat-conducting member including an access passageway between the upper air flow path and the lower air flow path. The mass of high heat conductivity material preferably comprises tangled batts of metal threads. In preferred variants of these electronic heater/humidifiers described above, the lower compartments comprise an upstream compartment, a pair of intermediate compartments and a downstream compartment, each such compartment including a water and air-porous horizontally-disposed, electrical heating element situated within the water reservoir, and a water- and air-porous vertically-disposed electrical heating element on the downstream side of each such compartment; the upstream compartment further including an air- and water-porous, electrically-insulating member upwardly vertically-spaced from the associated heater element, a vertically-disposed air- and water-porous, electrically-insulating member on the upstream side of the vertically-disposed air- and water-porous electrical heating element and a water-absorbent batt substantially filling such compartment; each such intermediate compartment including an air- and water-porous electrically-insulating member upwardly vertically-spaced from the heater element, a vertically-disposed air- and water-porous, electrically-insulating member on both the upstream and the downstream side of the vertically-disposed, air- and water-porous electrical heating element, and a water-absorbent batt substantially filling each such compartment; and the downstream compartment including an air- and water-porous, electrically-insulating member, upwardly vertically-spaced, from the heater element, a vertically-disposed air- and water-porous, electrically-insulating member, on the downstream side of the vertically-disposed air- and water-porous electrical heating element, and a water-absorbent batt substantially filling such compartment. The lower flow path is provided with a plurality of water absorbable batts, the batts preferably being made of a highly absorbent material, e.g. synthetic fibers.

The casing preferably is a heat insulated casing.

The heater/humidifier preferably includes a one-way flow valve connected to a heat insulated flexible outlet tube. Preferably, the outlet includes an oronasal mask connected to the one-way flow valve.

The heater/humidifier also include a thermal control module, connectable to the electric heaters. The module preferably includes a connection to a source of low voltage D.C. and a high-limit thermal sensor which turns heating power "on" or "off". The heater/humidifier includes thermal sensor means to sense the temperature of the air in the outlet tube. The module includes means to display that temperature in that outlet tube. Finally, the module includes means to maintain the temperature within a predetermined range.

As noted above, the present invention is a device for the treatment of hypothermic humans. It is based on the established principle of inhalation rewarming. This novel device is designed so that inspired air is heated and humidified as it is drawn through electrically-heated (12-Volt) wire coils and hydrophilic batts that are saturated with water. Optimum temperature of the inhalate is thermostatically controlled.

The novel arrangement of the materials comprising the heat-exchanger is strategic to efficient energy transfer from the battery source to the heat content of the inhalate. A water-saturated inhalate of about 43° to about 45° C. temperature can be maintained for at least one hour with a small, portable, 6 amp-hour battery. This is sufficient time to stabilize a victim against "afterdrop" of core body temperature, and to initiate rewarming.

BRIEF DESCRIPTION OF THE DRAWINGS

In the accompanying drawings.

Figure 1:
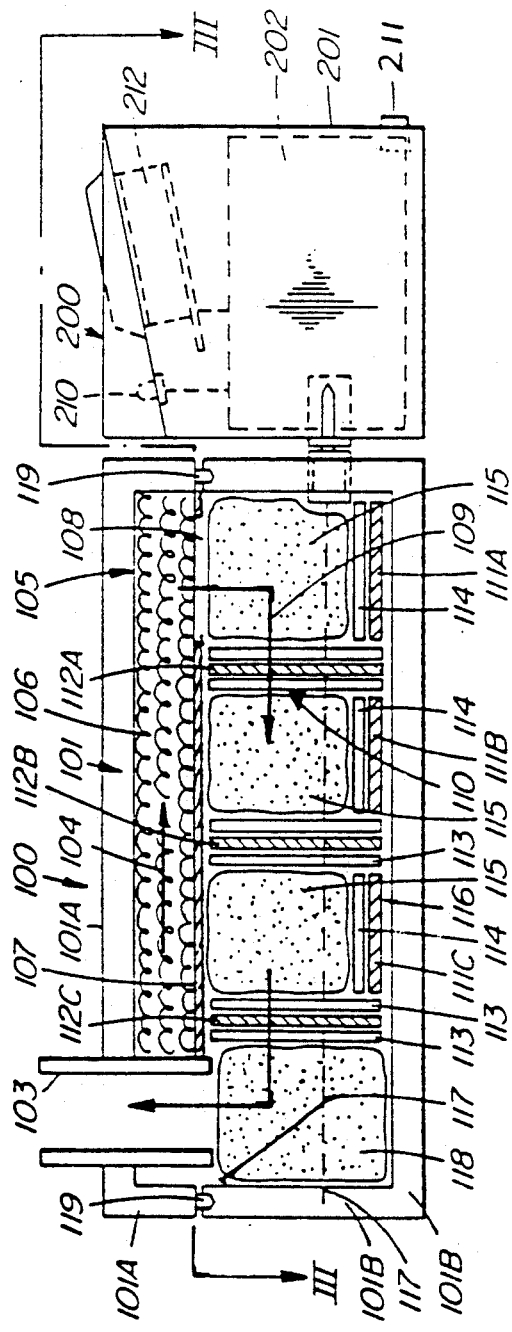
FIG. 1 is a central longitudinal partial sectional and partial elevational view of a heater/humidifier according to one embodiment of this invention.
Figure 2:
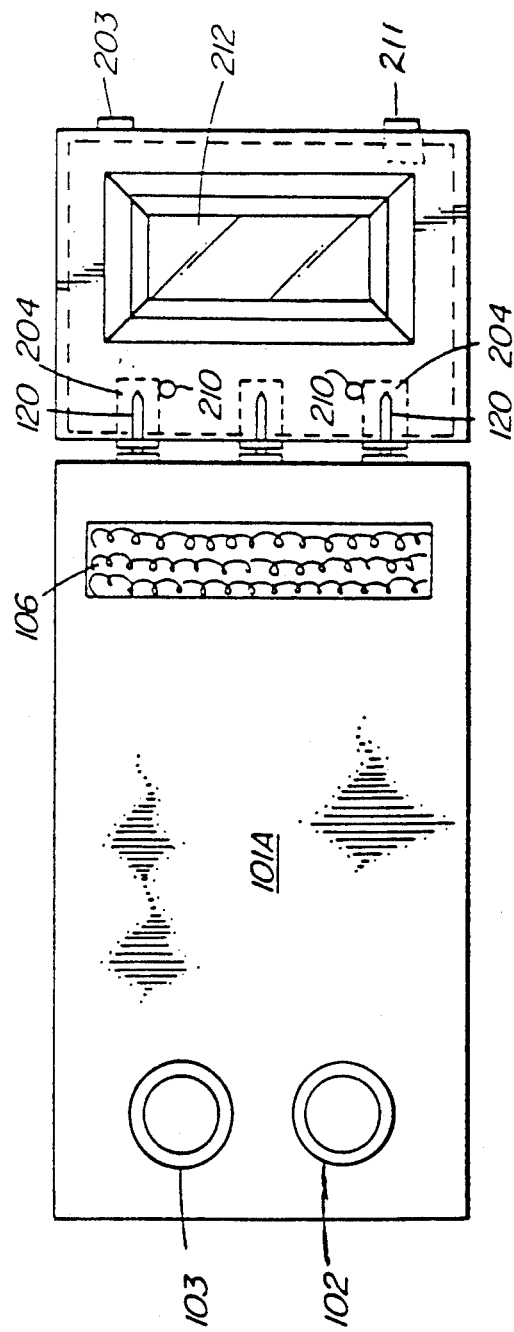
FIG. 2 is a top plan view thereof.
Figure 3:
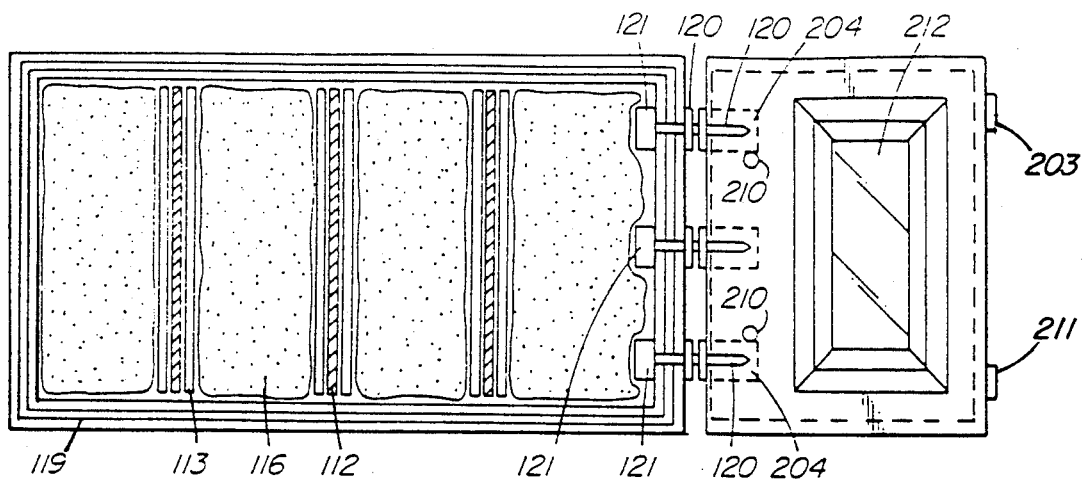
FIG. 3 is a section along the line III—III of FIG. 1.

DESCRIPTION OF PREFERRED EMBODIMENTS (i) Description of FIGS. 1, 2 and 3

Figure 4:
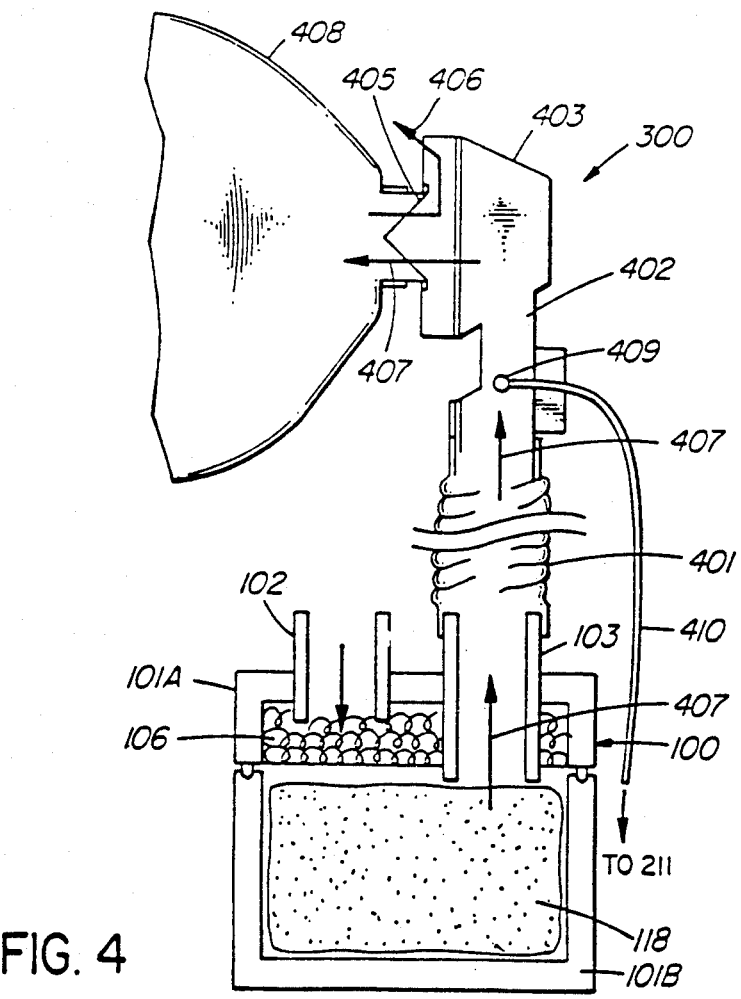
FIG. 4 is a partial sectional and partial end view of the heater/humidifier of this embodiment of this invention.

The heater/humidifier of this embodiment of this invention includes as prime components a heat exchanger module 100, a thermal control module 200 (See FIGS. 1, 2 and 3) and a one-way-flow airway system 300 (See FIG. 4).

The heat exchanger module 100 comprises a thermally insulated casing 101, preferably of rectangular parallelepiped form, and having an inlet port 102 and an outlet port 103. Inlet port 102 leads to an upper, forward-direction, flow path, (shown by arrow 104) in an upper heat exchanger chamber 105. To preheat the incoming air, chamber 105 is loaded with a tangled mass of high heat conductivity material 106, e.g. metal strands. The floor 107 of chamber 105 is made of a high heat conductive material, e.g. a metal, for example aluminum, copper, etc., and is provided with an outlet opening 108.

Outlet 108 leads to a lower, reverse-direction flow path, (shown by arrow 109) in a lower heat exchanger chamber 110. Lower heat exchanger chamber 110 is fitted with a plurality, e.g. three, horizontally-oriented, electric heater elements 111A, 111B, 111C, and a plurality, e.g. three, spaced-apart vertically-oriented heater elements 112A, 112B, 112C. Heater elements 111A, 111B, 111C and 112A, 112B, 112C each preferably are in the form of electrical windings around a porous, electrically-insulating board, which structure allows maximal exposure of air flowing through lower heat exchanger chamber 110 to the heated electrical wiring of the three, vertically-oriented heater elements 112A, 112B, 112C. Heating elements 112A, 112B, 112C are covered on each of their faces with a vertically-oriented, air-porous, electrically insulating member 113, while heating elements 111A, 111B, 111C are covered on their upper faces by horizontally-oriented, porous, electrically insulating member 114.

Within the spaces between members 113 are batts 115 of porous, hydrophilic material, e.g. absorbent synthetic fiber.

The bottom of the casing 101 provides a water reservoir 116.

The lower heat exchanger chamber 110 includes an outlet heat exchanger chamber 117 within which is a batt 118 of porous hydrophilic material, e.g. absorbent synthetic fiber.

It is preferred that the casing 101 be made in two parts, i.e. upper part 101A and lower part 101B, hermetically held together at sealing member 119.

The thermal control module 200 includes a casing 201 within which is appropriate thermostatic circuitry, well known to those skilled in the art and shown by block 202. The thermal control module 200 is connectable by means of the power terminal 203 to a source of 12 V D.C. electricity. The power is connectable to the electrical heaters 111A, 111B, 111C and 112A, 112B 112C by means of male plugs 120 on heat exchanger module 100 and female plugs 204 within the thermal control module 200. The thermal control module 200 also provides connection to high-limit thermal sensors 121 in heat exchanger module 100 to turn the heaters 111A, 111B, 111C and 112A, 112B, 112C "on" or "off" as indicated by indicator lights 210. The thermal control module 200 is also provided with a thermal input terminal 211 connected internally to thermal sensor 121, and with a digital display 212, of well-known construction.

(ii) Description of FIG. 4

The outlet 103 is connected to the one-way-flow airway system 300 as shown in FIG. 4. The outlet 103 is connected to a thermally-insulated airway 401, which is connected to the inlet 402 of a one-way valve 403, which is constructed to direct exhaled air to the environment through outlet 405, (as shown by arrow 406), and to direct inhaled air to be drawn through the heat exchanger module 100 (as shown by arrows 407). One way valve 403 is connected to an oronasal mask 408. Within airway 401 is an inhalate thermal sensor 409 which is connected, via line 410 to thermal input terminal 211.

OPERATION OF PREFERRED EMBODIMENT

To summarize, and as previously described, the present invention consists of three major sections: (A) a one-way-flow airway system; (B) a two-compartment heat exchanger; and (C) a thermal control module. It operates as follows:

To provide for humidification of the inhalate, approximately 50 ml of sterile water is added to the insulated heat exchanger through the inlet connector. The water will flow through the metal strands of the upper compartment of the heat exchanger and drip into the lower compartment through the passageway between the upper compartment and the lower compartment. It will then fill the bottom (reservoir) of the lower compartment, covering the horizontal heater elements and the lower portions of the vertical heater elements. The water will also "wick" into the porous, hydrophilic batts located between the vertical heater elements. The batts are separated from the heater elements by porous protectors which prevent direct contact between the batts and the heater elements.

To initiate warm-up of the heat exchanger, the thermal control module is attached to the heat exchanger and 12-Volt DC electricity is connected to the power terminal. Current flows to the three heater elements in the preferred embodiment (but a greater number of heater elements may be used if the heat exchanger is enlarged), thereby heating the contents of the lower compartment and, by conduction, heating the metal strands of the upper compartment. Warm-up requires about 2-4 minutes and overheating is prevented by monitoring heat exchanger temperature with the high-limit thermal sensor which turns heating power "on" or "off" as shown by the indicating lights.

The device is now ready for use by a person requiring heat therapy via the respiratory tract. The oronasal mask is held to the face. The one-way-flow valve directs exhaled air to the environment and inhaled air is drawn through the heat exchanger along the path (shown by the arrows). Air enters the exchanger through the inlet connector, and is pre-heated as it passes longitudinally through the metal strands of the upper compartment. It then flows through the passageway between the upper compartment and the lower compartment to the lower compartment. The air is further heated and is humidified to near saturation as it flows longitudinally through the porous heating elements, the porous protectors, and the hydrophilic batts of the lower compartment.

The air is directly heated by the vertical heater elements. The horizontal heater elements have no significant air flow through them, and instead, donate most of their heat to the water in the bottom of the compartment.

The warm, humid air then flows to the airway system through the outlet connector which passes through the upper compartment. This warm, humid air then passes through an insulated flexible tube which is connected to the one-way-flow valve. At this point of connection, an inhalate thermal sensor is located in the air stream. The temperature of the inhalate is fed back to the thermal control module by a sensor cable which is connected to the thermal input terminal. Inhalate temperature is shown continuously on the digital display, and appropriate thermostatic circuitry turns the heater elements on or off according to settings which are usually in the range of about 43° to about 45° C. Thus, warm and humid inhalate is provided for heating of a patient's body core.

In situations where a spontaneously breathing patient also needs oxygen therapy along with heat therapy, a supply of oxygen (not shown) via a demand valve from a compressed source can be joined to the inlet connector.

For a patient who is apnoeic, positive-pressure ventilation with air or oxygen is feasible because the heat exchanger is a sealed unit. A bag-resuscitator or respirator can be joined to the inlet connector and positive pressure ventilation with warm, humid air or oxygen will be provided. Where these ventilators are not available, a rescuer can force his/her exhaled air through the heat exchanger by exhaling into the inlet connector as in the manner of mouth-to-mouth resuscitation.

In situations where forced ventilation is being used, delivery of warm, humid air or oxygen to the patient can be by tracheal intubation simply by replacing the oronasal mask with an endotracheal tube.

After use of the device, cleaning and/or sterilization is facilitated by the above-described modular design. The airway system is disconnected from the heat exchanger and is able to be cleaned by standard procedures. The thermal control module, which does not need sterilization, can be removed from the heat exchanger by separating simultaneously the three, single-pin connectors. The heat exchanger is designed such that the upper and lower compartments are held together by suitable means. A seal ensures an air-tight union. For cleaning and sterilization, the two compartments are separated. The hydrophilic batts are removed from the lower compartment. Both compartments can now be cleaned and/or sterilized by standard methods. New hydrophilic batts can be replaced in the lower compartment and the device can then be assembled for future use.

The differences of the device of the present invention from existing technology are:

a) It differs from a commercially-available device in that it does not produce steam which then has to be cooled with ambient air by use of a special mixing valve.

b) It differs from most heater-humidifier devices for respiratory therapy in that it does not require compressed gas sources or fan-activated air flow.

c) It routes air through heated metal electric wire coils which are in proximity to a water-laden "fabric" (hydrophilic batts). The source of energy for heating the electric wire coils is electricity (12-volt DC battery power).

d) Efficiency of design allows the heat-exchanger to operate at a relatively low temperature (e.g. 50°-55° C.) compared to the other devices. This is a desirable safety feature in the event of accidental spillage of water from the device.

Advantages of this invention are:

a) The highly-efficient use of battery power by this device means that it can be satisfactorily operated by batteries that are small and light enough to be carried easily by a rescuer. This permits use of the device in remote, first-aid situations where motorized vehicles are not available (e.g. where search teams find a lost hiker, skier, etc.).

b) Effective therapy can be provided by the use of a battery energy source, thereby potentiating portability (independent of mains electrical power) which is often essential to first aid treatment of hypothermia.

c) An electrified device permits thermostatic control of exchanger temperature and inhalate temperature.

d) An electrified device permits digital electronic display of inhalate temperature.

e) 12-volt battery power is widely-available, especially in rescue vehicles (automobiles, boats, airplanes, helicopters).

f) The device is readily adaptable to heating and humidifying a source of oxygen gas (either compressed or at atmospheric pressure).

g) The device is also usable with a positive pressure, mechanical ventilation system (e.g. bag resuscitator or hospital respirator).

h) The energy source (battery) can be separated (by wires) from the heat source (coils), thereby allowing a smaller, lighter heat-exchanger. This provides greater convenience for positioning close to the mouth of the patient.

CONCLUSION

From the foregoing description, one skilled in the art can easily ascertain the essential characteristics of this invention, and without departing from the spirit and scope thereof, can make various changes and modification of the invention to adapt it to various usages and conditions. Consequently, such changes and modifications are properly, equitably, and "intended" to be, within the full range of equivalence of the following claims.

We claim:

1. An electronic heater/humidifier for hypothermia treatment comprising a casing provided with (a) a heat exchanger system comprising an upper compartment loaded with a tangled mass of high heat conductivity material, and serially-interconnected thereto, at least two serially-interconnected lower compartments, each such lower compartment being open at the bottom to a water reservoir and containing at least one heater element for heating water in the water reservoir, and a porous hydrophilic batt;

(b) an air flow path between an air inlet and an air outlet providing a one-way-flow airway system comprising an upper air flow path through said tangled mass of high heat conductivity material in said upper compartment, to transfer heat obtained conductively from the heater elements for preheating the incoming air, and a lower air flow path through said at least two porous hydrophilic batts, for transferring heated water to the site of vaporization in the air flow path by wicking action;

c) an inhalate thermal sensor located within the air stream of the air outlet, to monitor continuously the temperature of said air stream; and (d) heater control mean including a high-limit thermal sensor to control electric power to said electric heaters, dependent on the temperature sensed by said inhalate thermal sensor.

2. The electronic heater/humidifier of claim 1 wherein said air flow path includes an upper, forward direction air flow path through said upper compartment and a lower, reverse direction air flow path through said at least two lower compartments.

3. The electronic heater/humidifier of claim 1 wherein said upper air flow path is separated from said lower air flow path by a non-porous, heat-conducting member, said non-porous heat-conducting member including an access passageway between said upper air flow path and said lower air flow path.

4. The electronic heater/humidifier of claim 1 wherein said mass of high heat conductivity material comprises tangled batts of metal threads.

5. The electronic heater/humidifier of claim 4 wherein said lower compartments comprise: an upstream compartment, a pair of intermediate compartments and a downstream compartment; each said compartment including a water- and air-porous, horizontally-disposed, electrical heating element situated within said water reservoir, and a water- and air-porous, vertically-disposed, electrical heating element on the downstream side of each said compartment; said upstream compartment further including an air- and water-porous, electrically-insulating member, upwardly vertically-spaced from said air- and water-porous electrical heater element, a vertically-disposed, air- and water-porous, electrically-insulating member, on the upstream side of said vertically-disposed, air- and water-porous, electrical heating element and a water-absorbent batt substantially filling said compartment; each said intermediate compartment including an air- and water-porous, electrically-insulating member upwardly vertically-spaced from said air- and water-porous electrical heater element, a vertically-disposed, air- and water-porous, electrically-insulating member on both the upstream and the downstream side of said vertically-disposed, air- and water-porous electrical heating element, and a water-absorbent batt substantially filling each said compartment; and said downstream compartment including an air- and water-porous, electrically-insulating, member, upwardly vertically-spaced from said air- and water-porous electrical heater element, a vertically-disposed, air- and water-porous, electrically-insulating member on the downstream side of said vertically-disposed, air- and water-porous electrical heating element and a water-absorbent batt substantially filling said compartment.

6. The electronic heater/humidifier of claim 5 wherein said water-absorbent batts are made of absorbent synthetic fiber material.

7. The electronic heater/humidifier of claim 1 wherein said lower compartments comprise: an upstream compartment, a pair of intermediate compartments and a downstream compartment; each said compartment including a water- and air-porous, horizontally-disposed electrical heating element situated within said water reservoir, and a water- and air-porous, vertically-disposed, electrical heating element on the downstream side of each said compartment; said upstream compartment further including, and air- and water-porous, electrically-insulating member, upwardly vertically-spaced from said heater element, a vertically-disposed, air- and water-porous, electrically-insulating member on the upstream side of said vertically-disposed air- and water-porous, electrical heating element, and a water-absorbent batt substantially filling said compartment; each said intermediate compartment including an air- and water-porous, electrically-insulating member upwardly vertically-spaced from said heater element, a vertically-disposed, air- and water-porous, electrically-insulating member on both the upstream side and the downstream side of said vertically-disposed, air- and water-porous, electrical heating element, and a water-absorbent batt substantially filling each said compartment; and said downstream compartment including an air- and water-porous, electrically-insulating member, upwardly vertically-spaced from said heater element, a vertically-disposed, air- and water-porous, electrically-insulating member on the downstream side of said vertically-disposed, air- and water-porous, electrical heating, element and a water-absorbent batt substantially filling said compartment.

8. The electronic heater/humidifier of claim 7 wherein said water-absorbent batts are made of absorbent synthetic fiber material.

9. The electronic heater/humidifier of claim 1 wherein said casing is a heat insulated casing.

10. The electronic heater/humidifier of claim 1 including a one-way flow valve connected to a heat insulated flexible outlet tube connected to said air outlets.

11. The electronic heater/humidifier of claim 10 including an oronasal mask connected to said one-way flow valve.

12. The electronic heater/humidifier of claim 10 including thermal sensor means to sense the temperature of the air in the said heat-insulated, flexible, outlet tube.

13. The electronic heater/humidifier of claim 12 including means connected to said thermal sensor means to display the temperature of the air inhalate, and control means to maintain said temperature within a predetermined range by switching said electric heater means "on" or "off" dependent on the temperature sensed by said thermal sensor.

14. The electronic heater/humidifier of claim 13 including a thermal control module, connectable to said electric heaters, said module including a connection to a source of low voltage D.C. and a high-limit thermal sensor to effect said switching of said heating power "on" or "off".

* * * * *